United States Patent
Bauer

(10) Patent No.: US 7,547,413 B2
(45) Date of Patent: Jun. 16, 2009

(54) SYSTEMS AND METHODS FOR DISINFECTING AND STERILIZING BY APPLYING STEAM VAPOR CONTAINING LOW ZETA POTENTIAL MINERAL CRYSTALS

(75) Inventor: Walter J. Bauer, Baden (CA)

(73) Assignee: Bauer Energy Design, Inc., Baden, ON (CA)

(*) Notice: Subject to any disclaimer, the term of this patent is extended or adjusted under 35 U.S.C. 154(b) by 0 days.

(21) Appl. No.: 11/350,293

(22) Filed: Feb. 7, 2006

(65) Prior Publication Data
US 2006/0177342 A1 Aug. 10, 2006

Related U.S. Application Data

(60) Provisional application No. 60/651,042, filed on Feb. 7, 2005.

(51) Int. Cl.
*A61L 2/07* (2006.01)
(52) U.S. Cl. .......................................... 422/22; 422/298
(58) Field of Classification Search ........................ None
See application file for complete search history.

(56) References Cited

U.S. PATENT DOCUMENTS

| | | | |
|---|---|---|---|
| 3,933,606 A | 1/1976 | Harms | |
| 4,342,730 A * | 8/1982 | Perrotta | 423/215.5 |
| 4,772,369 A | 9/1988 | Mercier et al. | |
| 5,246,586 A | 9/1993 | Ban et al. | |
| 5,591,317 A | 1/1997 | Pitts, Jr. | |
| 5,695,644 A | 12/1997 | Buchanan et al. | |
| 5,817,224 A | 10/1998 | Pitts, Jr. | |
| 5,906,800 A * | 5/1999 | Napierkowski et al. | 422/298 |
| 5,951,856 A | 9/1999 | Cho | |
| 6,679,988 B2 | 1/2004 | Gsell | |
| 6,689,270 B1 | 2/2004 | Evert | |
| 6,849,178 B2 | 2/2005 | Hecking | |
| 2001/0035342 A1 * | 11/2001 | Morse et al. | 204/164 |

FOREIGN PATENT DOCUMENTS

| | | | |
|---|---|---|---|
| AU | 580474 | * | 1/1987 |
| DE | 41 00 799 A1 | | 7/1992 |
| GB | 1 288 552 | | 9/1972 |
| WO | 95/15922 A1 | | 6/1995 |
| WO | 98/46533 A1 | | 10/1998 |

* cited by examiner

*Primary Examiner*—Elizabeth L McKane
(74) *Attorney, Agent, or Firm*—Ann W. Speckman; Victor N. King; Speckman Law Group PLLC

(57) ABSTRACT

Methods and systems for generating steam vapor having low zeta potential mineral crystals capable of disinfecting surfaces and objects upon an exposure period to the steam vapor. The steam vapor system comprises an aqueous liquid source having a threshold concentration of selected minerals, a liquid treatment system for treating the aqueous source liquid to produce treated liquid having an enhanced concentration of low zeta potential mineral crystals, and a steam vapor generator for producing steam vapor from the treated liquid, whereby the steam vapor has a higher concentration of low zeta potential mineral crystals than the aqueous liquid source. The steam vapor generated from the treated liquid is applied to surfaces or objects.

18 Claims, 5 Drawing Sheets

Calcium carbonate crystals from untreated water

Figure 1:
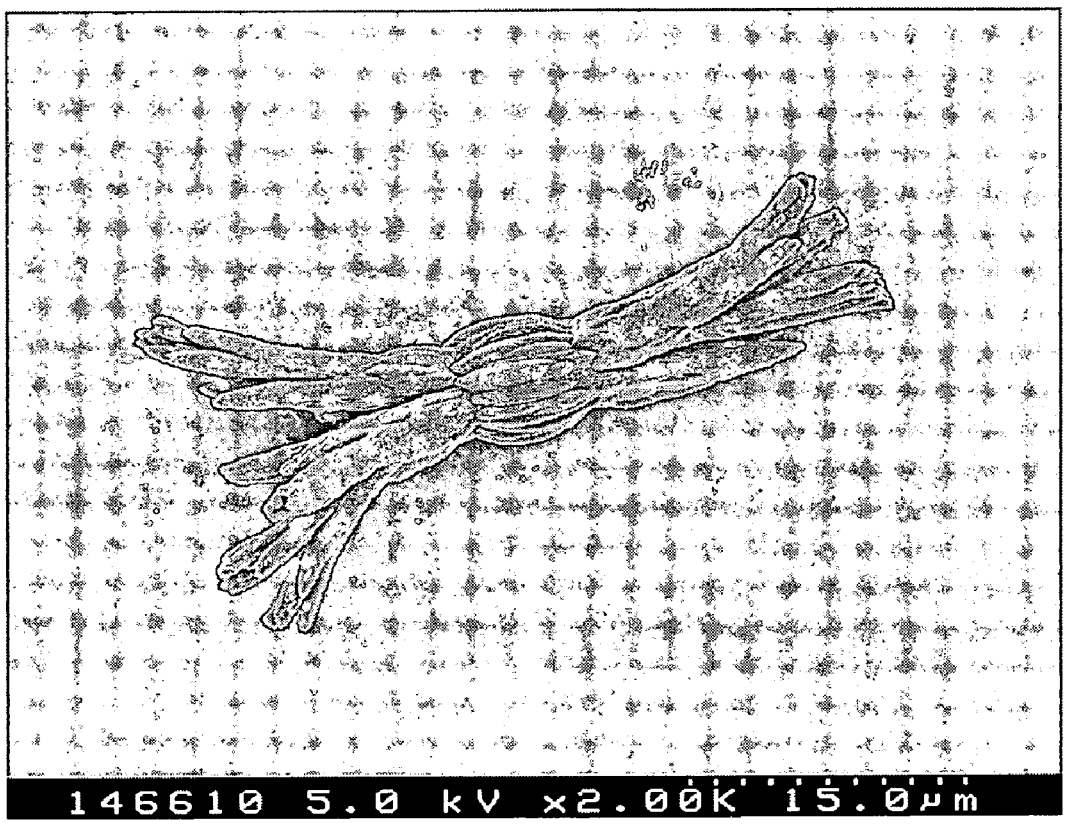

Calcium carbonate crystals from the treated water

SYSTEMS AND METHODS FOR DISINFECTING AND STERILIZING BY APPLYING STEAM VAPOR CONTAINING LOW ZETA POTENTIAL MINERAL CRYSTALS

CROSS REFERENCE TO RELATED APPLICATION

This application claims priority under 35 U.S.C. §119(e) to U.S. Provisional Application No. 60/651,042, filed Feb. 7, 2005.

FIELD OF THE INVENTION

The present invention generally relates to systems and methods for disinfection and sterilization by application of steam vapor containing low zeta potential crystals.

BACKGROUND OF THE INVENTION

Disinfection generally involves the use of a chemical agent and/or procedure to inhibit the activity of, and preferably, substantially eliminate virtually all recognized pathogenic microorganisms. Most disinfectants do not necessarily eliminate all microbial forms (e.g., bacterial endospores), and many have toxic side effects. In general, three levels of disinfection are recognized: high, intermediate, and low. High-level disinfection eliminates all organisms, with the exception of high levels of bacterial spores. Intermediate-level disinfection eliminates mycobacteria, most viruses, and bacteria. Low-level disinfection eliminates some viruses and bacteria.

Disinfectants can be quite expensive and are costly for long term, frequent applications. Also, since many disinfectants are rapidly inactivated by organic matter, objects that are to be disinfected usually need to be cleaned thoroughly with warm water and detergent prior to disinfection, which can be time-consuming. In addition, some disinfectants are toxic and therefore are potentially dangerous and hazardous to humans.

Sterilization involves the use of a physical or chemical procedure to substantially destroy all forms of microorganisms (cells, pathogens, viruses, bacteria, fingi, spores, and molds), including highly resistant bacterial endospores. Common sterilizing systems and methods include the use of moist heat by steam autoclaving, ethylene oxide gas, dry heat, and chemical vapor.

Steam autoclaving has the advantages of providing relatively rapid turnaround time, low cost per cycle, and it does not require the use of toxic chemicals. However, due to moisture and generally high temperature operation, steam autoclaving may degrade instruments and cannot be used with many plastics. Steam autoclaving also requires the use of distilled, deionized water, which is difficult to generate and can become expensive. Other disadvantages of steam autoclaving include: the high-cost of an autoclave unit, the need for a relatively large area of space to place the autoclave, and the need for constant maintenance.

Sterilization using ethylene oxide gas (ETO) requires relatively low temperatures and can be quite effective to inactivate or kill microbial cells. ETO's small molecular size also allows penetration into minute openings and porous substances, allowing sterilant into areas that may not normally receive exposure from other methods of sterilization. However, ETO vaporizes at room temperature and is therefore difficult to contain. It is also extremely explosive unless mixed with other gases. In addition to the problems stemming from ETO's molecular structure, its molecular activity can enable it to combine with many other materials (and/or chemicals) to form new compounds. One hazard of employing ETO is that during sterilization it can easily penetrate thin layers of most plastics and virtually all medical devices. Further, an ETO sterilization cycle can take up to two to three hours and a lengthy aeration time must follow each cycle.

Sterilization by dry heat is generally conducted in an oven equipped with forced air circulation. The heat destroys microorganisms by causing irreversible damage to the cellular components. A typical sterilization process with dry heat is performed at high temperatures (e.g. 160° C. for 2 hours). The challenge in dry heat sterilization is to obtain and maintain an even, high temperature distribution among the goods being sterilized. Furthermore, dry heat sterilization is a very time-consuming process and cannot be used with plastics.

Chemical vapor sterilization generally does not cause corrosion and rusting, and objects sterilized using chemical vapor are dry at the end of the sterilization cycle. However, chemical vapor sterilization generally uses toxic chemicals, which require specialized and vigorous handling and ventilation requirements.

Various water treatment technologies are known and used in the art. U.S. Pat. No. 5,591,317 discloses an electrostatic-field generator for use in water treatment that consists of a vitrified ceramic tube of unibody construction having a single open end adapted to receive a high-voltage power cable through an insulated cap. The interior surface of the ceramic tube is lined with a layer of conductive material electrically connected to the power cable, thereby providing a relatively-large conductive surface in intimate contact with the dielectric surface of the ceramic tube. In operation, the device is immersed in a body of water connected to ground and the power cable is energized with a high DC voltage, thereby creating an electrostatic field across the dielectric of the tube's ceramic and across the body of water. Because of the difference in the dielectric coefficients of the materials, the majority of the applied potential is measured across the water, thus providing the desired electrostatic effect on its particulate components.

U.S. Pat. No. 5,817,224 discloses a method for enhancing the efficiency of a solid-liquid separation process by using an electrostatic-field generator that utilizes a vitrified ceramic tube of unibody construction having a single open end adapted to receive a high-voltage power cable through an insulated cap. The interior surface of the ceramic tube is lined with a layer of conductive material electrically connected to the power cable, thereby providing a relatively-large conductive surface in intimate contact with the dielectric surface of the ceramic tube. The device is used in connection with conventional chemical additives for separating suspended solids from water to reduce chemical consumption and improve operating efficiency. The device is immersed in the water carrying suspended particles upstream of the treatment with chemical agents and is energized with a high DC voltage, thereby creating an electrostatic field across the dielectric of the tube's ceramic and across the body of water. The charge on the surface of particles to be separated by physical aggregation is altered by the electrostatic field so generated and is manipulated so as to produce enhanced performance by the chemicals used in the conventional process downstream.

U.S. Pat. No. 4,772,369 discloses a process and an apparatus for treating water which comprises decomposing the minerals dissolved in the water into cations comprising ferromagnetic, paramagnetic and residual particles, and disaggregating the cations and anions by utilizing ferromagnetic particles as a temporary mobile anode facing a strong cathode and paramagnetic particles as a weak cathode. The disaggregated minerals form a dielectric layer on the strong cathode, which is extracted.

U.S. Pat. No. 6,679,988 discloses a water purification system for production of USP purified water and/or USP water for injection including a backwashable, chlorine tolerant microfilter or ultrafilter for initial filtration of the feed water. The filtrate from the filter is provided to a dechlorinator prior to being subjected to an optional, reverse osmosis membrane unit and then to a still which discharges purified water at USP standards for purified water or water for injection.

U.S. Pat. No. 6,689,270 discloses a water treatment apparatus reducing hard water deposits in a conduit. Water having dissolved salts therein causing scaling is treated by flowing through a passage in an elongate tubular member. The tubular member has a first metal inside surface exposed to the water. A second metal surface is positioned therein and the two surfaces have areas of 1:1 up to about 125% with the second metal being different from the first metal. The metal surfaces are electrically insulated from each other so that current flow between the two is through the water.

U.S. Pat. No. 6,849,178 discloses an apparatus for water treatment by means of an electrical field is provided with an anode and a cathode in at least one treatment chamber through which the water to be treated passes. The apparatus is characterized in that the at least one treatment chamber forms a prismatic space with an elongated cross section, the anode and the cathode are formed by pairs of parallel, stick-shaped electrodes which extend spaced apart into said space and a voltage is applicable between the electrodes. One end of the at least one treatment chamber is connected to a water inlet and the other end of the at least one treatment chamber is connected to a water outlet, whereby a waterflow from one electrode to the other is generated, which is substantially transverse to the longitudinal axes of the electrodes.

SUMMARY OF THE INVENTION

The present invention provides methods and systems for disinfection and sterilization using steam vapor having a generally high concentration of low zeta potential mineral crystals. The inventive system treats source liquid in a low zeta potential crystal generator, thereby changing the crystalline structure of minerals such as calcium carbonate ($CaCO_3$) in the source liquid, and enhancing the concentration of low zeta potential crystals in the liquid. The source liquid solution is preferably water, but other aqueous solutions may be used as source liquids. The treated liquid is typically heated to generate wet or dry steam vapor for disinfection and sterilization.

Low zeta potential crystal generators suitable for use in the present invention may comprise a passive electro mechanical device that catalyses the crystallization of minerals in liquid solutions. Zeta potential is the electrical potential that exists across the interface of all solids and liquids. Almost all particulate or macroscopic materials in contact with a liquid acquire charges on their surfaces. Zeta potential is an important and useful indicator of these charges and can be used to predict and control the stability of colloidal suspensions or emulsions. The lower the zeta potential, the more likely the suspension is to be stable because the charged particles repel one another and thus overcome the natural tendency to aggregate.

Calcium carbonate ($CaCO_3$) is generally present in at least moderate concentrations in water. In methods and systems of the present invention, calcium carbonate ionic species in the source liquid solution are crystallized to produce aragonite.

$$Ca^{2+}+CO_3^{2-}\rightarrow CaCO_{3(s)(aragonite)}$$

Aragonite is a common carbonate mineral and a polymorph of calcite. In other words, aragonite has the same chemistry as calcite but it has a different structure, and more importantly, different symmetry and crystal shapes. Aragonite's more compact structure is composed of triangular carbonate ion groups ($CO_3$), with a carbon at the center of the triangle and the three oxygens at each corner. Unlike calcite, the carbonate ions of an aragonite do not lie in a single plane pointing in the same direction. Instead, they lie in two planes that point in opposite directions, thereby destroying the trigonal symmetry that is characteristic of calcite's structure. Aragonite crystal formation and the conditions of the aragonite crystal growth are such that cations other than calcium are entrapped within the crystal lattice. This condition modifies the distribution of the charge at the surface of the crystals and lowers the zeta potential of the crystals. Minerals other than calcium carbonate may also be induced to form low zeta potential crystals.

One exemplary low zeta potential crystal generator suitable for use in methods and systems of the present invention is known as the "Turbu-Flow™" treatment system. The Turbu-Flow™ system is well known in the art and is described, for example, in Australia Patent No. 580474. The principle by which the Turbu-Flow™ system operates is a surface electro-chemical reaction between the crystalline particles which exist in a source liquid and the special alloy elements forming the core of the Turbu-Flow™ system.

The Turbu-Flow™ treatment system comprises a stack of metal alloy conditioning discs. The liquid flow path through the unit maximizes turbulent flow over the surfaces of the conditioning elements. The discs are constructed of metal alloys selected from two groupings of metals of opposite electro-negativity. When an ion-laden liquid solution contacts the elements, the ions are attracted onto the elements, causing them to become neutralized. The turbulence of liquid flow facilitates neutralization of the ionic species and removal of the ions as neutral particles in a harmless colloidal suspension.

The density of crystal seeds produced by a low zeta potential crystal generator such as the Turbu-Flow™ system is generally high, and the continued growth of the crystals formed in the treated liquid is prevented because of the rapid drop in the calcium (and other minerals) ion concentrations in the treated liquid. The crystals generated thus remain at a size in the range of nano size particles (generally from 1 to 999 nm). The Turbu-Flow™ system's effect on crystal structure and formation and the difference in low zeta potential crystal composition between untreated liquids and liquids treated with the Turbu-Flow™ system was not previously known.

In addition to observing that the zeta potential of crystals present in water treated by the Turbu-Flow™ system is substantially different from that of untreated water, it has been unexpectedly discovered that steam vapor produced using aqueous solution(s) having a relatively high concentration of low zeta potential mineral crystals is exceptionally effective in disinfecting and sterilizing surfaces and objects. Experimental results demonstrate that steam vapor produced using aqueous solutions having a relatively high concentration of low zeta potential mineral crystals effectively eliminated a variety of microbial populations in relatively short exposure periods of thirty (30) seconds or less.

The methods and systems of the present invention utilize a source liquid solution, such as tap water, municipal water, and the like, containing minerals. In one embodiment, the source liquid may be treated prior to treatment in a low zeta potential crystal generator to remove contaminants such as debris, oils, and other substances that would interfere with the crystallization treatment. In another embodiment, the mineral composition of the source liquid may be determined prior to treatment of the liquid, and selected minerals may be added to the source liquid to facilitate and enhance crystal formation in the low zeta potential crystal generator.

The source liquid solution is treated by passage through the low zeta potential crystal generator to modify the crystal structure of minerals in the source liquid solution, providing treated liquid comprising a higher concentration of low zeta potential crystals than that found in the untreated source liquid. The low zeta potential crystals are preferably present in a relatively high concentration in the treated water and are small, preferably in the nano-size range. In a preferred embodiment, treatment of the source liquid in the low zeta potential crystal generator does not substantially alter the elemental composition of the source liquid. In a preferred embodiment, the concentration of elements such as barium, boron, calcium, copper, iron, magnesium, potassium, sodium, and the like in the untreated source liquid is substantially the same as the concentration of those elements in the treated liquid, although the concentration of low zeta potential crystals in the treated liquid is substantially higher than the concentration of low zeta potential crystals in the untreated source liquid.

The treated liquid solution containing an enhanced concentration of low zeta potential crystals is heated in a steam generator to produce steam vapor, and the steam vapor is distributed for use in connection with disinfection and sterilization. Steam vapor produced using liquid having a high concentration of low zeta potential crystals is extremely effective in destroying cells, pathogens, viruses, bacteria, fungi, spores, and molds.

In one embodiment, the source liquid treated by passage through a low zeta potential crystal generator, such as a Turbu-Flow™ system, containing a high concentration of low zeta potential crystals, is optionally passed through at least one filtration system, whereby bacteria, viruses, cysts, and the like are substantially removed from the treated liquid. Any filtration systems known in the art may be used and incorporated in the inventive system. Filtration systems may include, but are not limited to, particle filters, charcoal filters, reverse osmosis filters, active carbon filters, ceramic carbon filters, distiller filters, ionized filters, ion exchange filters, ultraviolet filters, back flush filters, magnetic filters, energetic filters, vortex filters, chemical oxidation filters, chemical additive filters, Pi water filters, resin filters, membrane disc filters, microfiltration membrane filters, cellulose nitrate membrane filters, screen filters, sieve filters, or microporous filters, and combinations thereof. The treated and optionally filtered liquid is heated in the steam generator to produce steam vapor containing an enhanced concentration of low zeta potential crystals, and the steam vapor is distributed for use in connection with disinfection and sterilization.

In another embodiment, the treated source liquid, before it reaches the optional filtration system, is optionally passed through a pre-filtration system, whereby minerals, such as iron, sulfur, manganese, and the like, are substantially removed from the treated source liquid. The treated and optionally pre-filtered liquid, containing a high concentration of low zeta potential crystals, may then be passed through the optional at least one filtration system, whereby bacteria, viruses, cysts, and the like are substantially removed from the treated and optionally pre-filtered liquid.

In yet another embodiment, the source liquid is treated by a first low zeta potential crystal generator. The treated liquid is optionally passed through the optional pre-filtration system and the optional at least one filtration system. The treated liquid may be distributed to and stored in a storage container, such as a reservoir. Before the stored treated liquid is heated in the steam generator to produce steam vapor, the stored liquid is optionally passed through a second low zeta potential crystal generator, whereby additional low zeta potential crystals are generated. The twice treated liquid is then heated in the steam generator to produce steam vapor containing an enhanced concentration of low zeta potential crystals, and the steam vapor is distributed for use in connection with disinfection and sterilization.

Any chelating agent, biocidal agent, fungicidal agent, surfactant, inorganic coagulant, polymeric coagulant, hydrophilic colloid known in the art may be added to or incorporated with the source liquid prior to treatment by the inventive system, the treated liquid, or the generated steam vapor.

Steam vapor containing an enhanced concentration of low zeta potential crystals generated by the inventive system and methods may be applied to various surfaces and objects, and the like, using a steam applicator, to disinfect and/or sterilize surfaces and objects, whereby cells, pathogens, viruses, bacteria, fungi, spores, molds, and the like are substantially reduced or eliminated. The steam vapor may also be introduced and applied to surfaces and objects in enclosed systems to disinfect and/or sterilize the surfaces and objects. These enclosed systems may include, but are not limited to, autoclaves, sterilizers, dishwashers, and the like.

BRIEF DESCRIPTION OF THE DRAWINGS

The present invention will be described in greater detail in the following detailed description, with reference to the accompanying drawings, wherein:

FIG. 1 shows a scanning electronic microscope (SEM) image of a calcium carbonate crystal obtained from untreated water;

FIG. 2 shows an SEM image of a calcium carbonate crystal obtained from water treated in a Turbu-Flow™ system;

FIG. 3 shows measurement results of zeta potential of particles in untreated water;

FIG. 4 shows measurement results of zeta potential of particles in water treated in a Turbu-Flow™ system; and FIG. 5 shows an embodiment of the inventive steam vapor system for disinfection and sterilization.

DETAILED DESCRIPTION OF THE INVENTION

The steam vapor generation system of the present invention may be constructed in a variety of different embodiments and may be employed in connection with disinfecting and sterilizing various kinds of surfaces and objects. Water sources, such as tap water, municipal water sources, and the like may be used as source liquid for the inventive system and treated to modify the crystal structure of minerals in the source liquid to produce treated liquid having a high concentration of low zeta potential crystals. The treated liquid is then heated in a steam generator to produce steam vapor, generally at temperatures exceeding 95° C. or 200° F. This steam vapor is highly effective in destroying microorganisms on surfaces and objects exposed to the steam after relatively short exposure times. The steam vapor generated by methods and systems of the present invention can be dry steam vapor or wet steam vapor.

Application of steam vapor generated using the treated liquid effectively disinfects and reduces or eliminates microbial populations on treated surfaces and objects without changing the elemental composition of the source liquid and without requiring the use of toxic or harmful additives. Steam vapor may be applied to various types of surfaces, including hard surfaces, textiles such as carpets, upholstery, and the like, in any environment, using a steam vapor applicator to expose surfaces, or objects, to the produced steam vapor. Disinfection using steam vapor application may be carried out indoors and outdoors, in enclosed or open spaces. The process and the steam vapor generated is non-toxic and the system is quiet and easy to operate. The system and process may be implemented in a stationary, installed unit, or in a portable unit. The inventive system may also be retrofit in existing steam vapor distribution systems. Although several specific embodiments are described, it will be apparent that the invention is not limited to the embodiments illustrated, and that additional embodiments may also be used.

Figure 2:
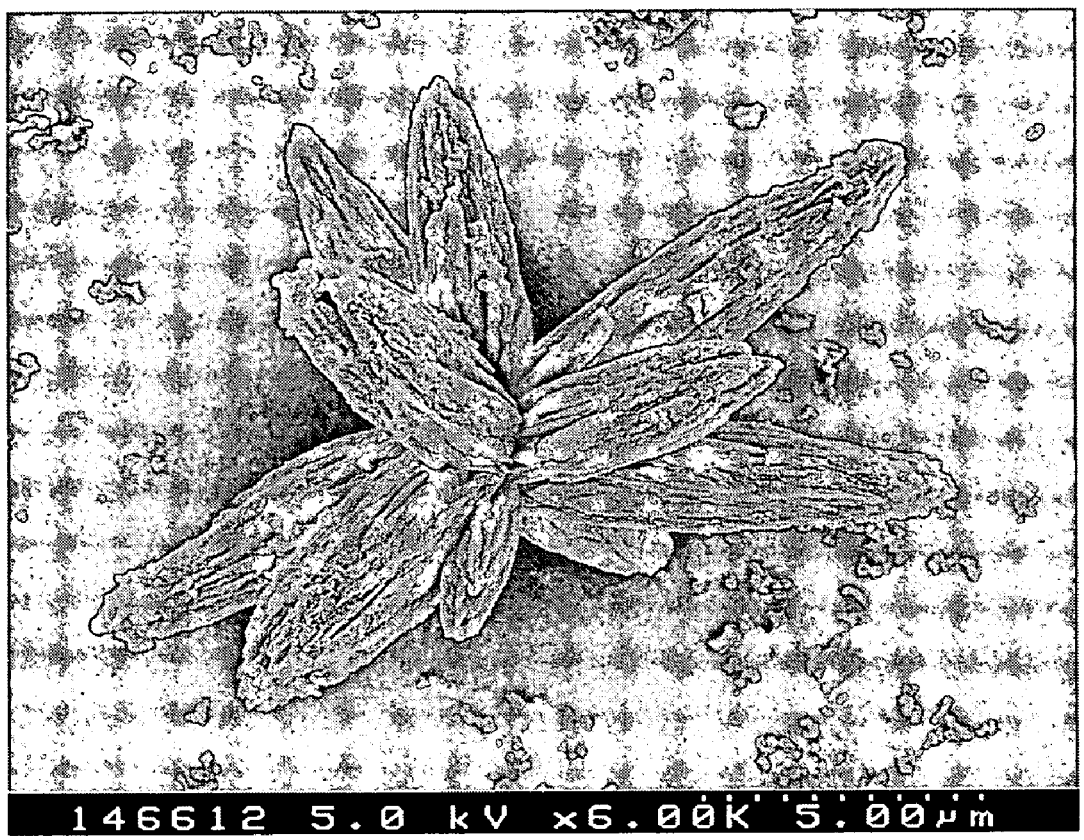

The inventive system incorporates a treatment module comprising a low zeta potential crystal generator. The low zeta potential mineral crystals produced after passage of source liquid through a low zeta potential crystal generator according to the inventive system are of a different structure and nature than the mineral crystals present in untreated liquid sources. FIG. 1 shows a scanning electron microscope (SEM) image of a calcium carbonate crystal obtained from an untreated water sample, and FIG. 2 shows an SEM image of a calcium carbonate crystal obtained from water following treatment in a Turbu-Flow™ system. The crystal structure of the calcium carbonate crystal (aragonite) obtained from water treated in a low zeta potential crystal generator, such as the Turbu-Flow™ system, is dramatically different from the crystal structure of calcium carbonate in the untreated water sample, as evidenced by the images of crystals in the untreated and treated water samples.

Zeta potential is a measurement of the electrical voltage difference between the surface of colloids and its suspending liquid. Zeta potential, measured generally by video under an electron microscope, is related to the actual speed of charged mineral particles in water traveling between an anode and cathode electrode in a direct electrical current field. Zeta potential is thus a direct measurement of electrophoretic mobility (EM). In general, electrophoretic mobility is expressed as microns/second per volts/centimeter. The first term, microns per second, is a velocity measurement. The second term, volts per centimetre, is an expression of the electric field strength. Electrophoretic mobility is, therefore, a relative measure of how fast a charged mineral particle in water moves in an electrical current field.

Zeta potential can be calculated from the measured electrophoretic mobility using a theoretical relation between the two that is dependent on the dielectric constant and the viscosity of the suspending liquid. Zeta potential is generally expressed in millivolts (mV) and generally measures between a range of 0 and +100 mV or 0 and −100 mV. The "plus" or "minus" signs of zeta potential measurements represent the positive or negative traveling direction of the particles in water, respectively, and do not relate to the actual value of the zeta potential. In other words, the value of zeta potential is irrespective of its "sign". Typical zeta potential of mineral particles in water measures between about −13 mV and −25 mV. The zeta potential of mineral crystals following treatment of the water in a low zeta potential crystal generator generally demonstrates a reduction of value towards 0 mV and measures between about 0 mV and −10 mV.

Figure 3:
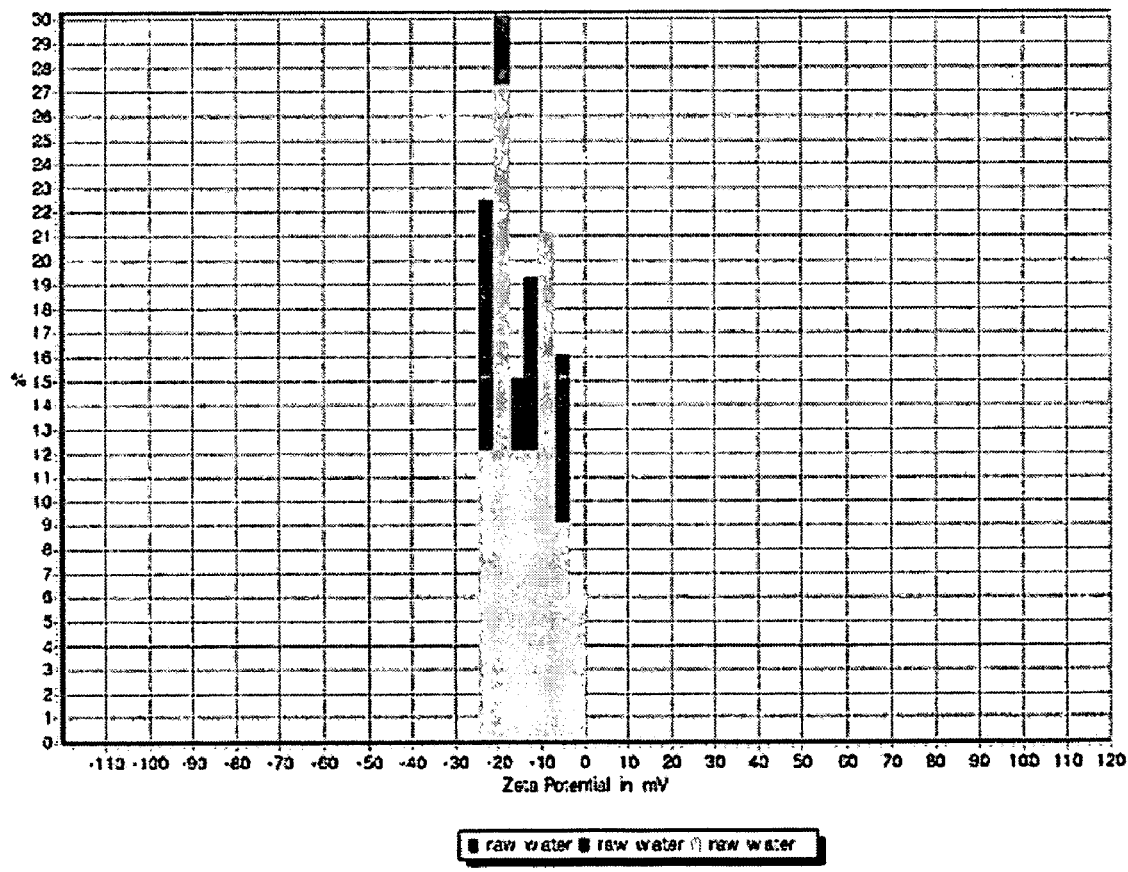
Figure 4:
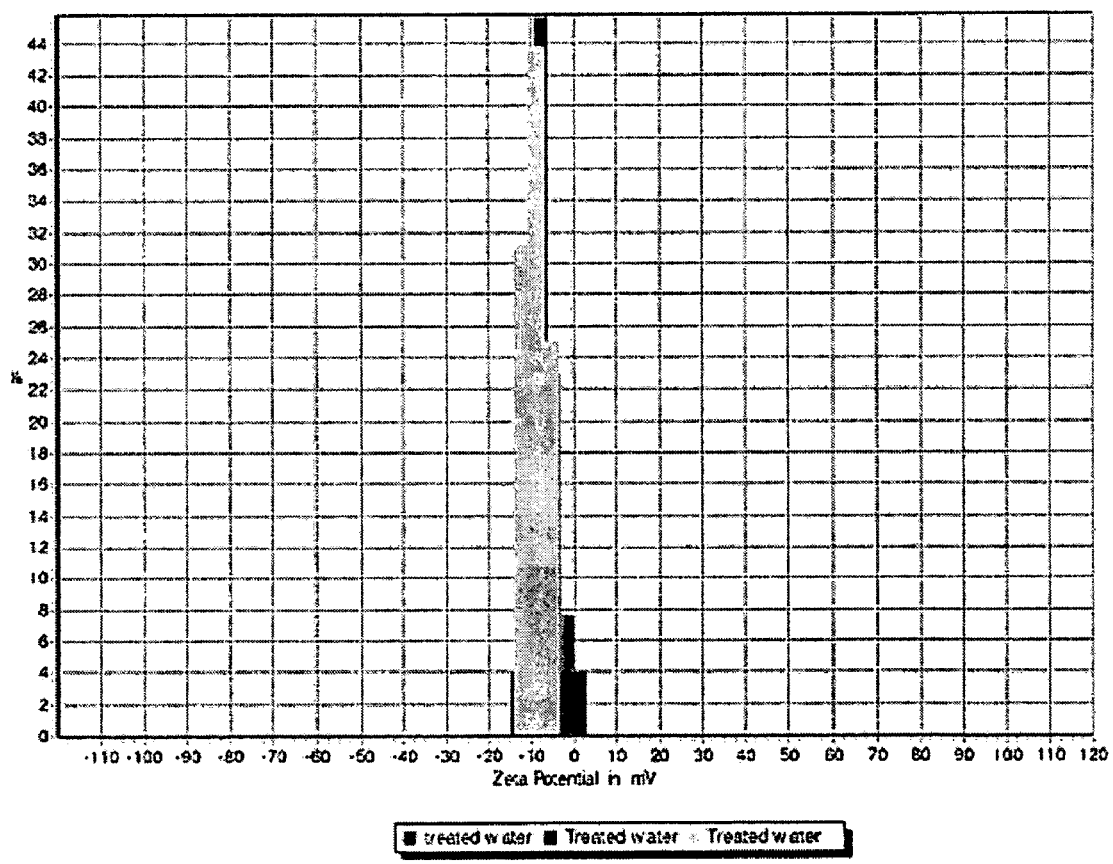

In one study, the zeta potential of mineral particles in untreated water and water from the same source treated by passage through a Turbu-Flow™ low zeta potential crystal generator was measured and compared. Results of the measurements are shown in FIG. 3 (untreated water) and FIG. 4 (treated water). The zeta potential of mineral particles in untreated water was measured, in three samples, as −14.50 mV, −14.65 mV and −13.53 mV. The zeta potential of mineral crystals in water from the same source following treatment by passage through a Turbu-Flow™ system was measured, in three samples, as −7.41 mV, −7.27 mV, and −8.84 mV. The study demonstrates that mineral particles in untreated water generally has a zeta potential measurement between a range of about −12 mV and −15 mV, and passage of the untreated water through a low zeta potential generator such as the Turbu-Flow™ system results in treated water containing mineral crystals that generally have a zeta potential measurement between a range of about −4 mV and −10 mV.

Thus, passage of water through a low zeta potential generator in a system of the present invention reduces the zeta potential of mineral particles by about 20% to 60%. In another embodiment, passage of water through a low zeta potential generator in a system of the present invention reduces the zeta potential of mineral particles by 25%. In yet another embodiment, passage of water through a low zeta potential generator in a system of the present invention reduces the zeta potential of mineral particles by 30%. In yet another embodiment, passage of water through a low zeta potential generator in a system of the present invention reduces the zeta potential of mineral particles by 40%. In still another embodiment, passage of water through a low zeta potential generator in a system of the present invention reduces the zeta potential of mineral particles by 50%. In an alternative embodiment, passage of water through a low zeta potential generator sin a system of the present invention reduces the mineral potential of mineral particles by 60%.

The source liquid solution to be treated in the low zeta potential crystal generator is preferably mildly "hard", and more preferably quite "hard." That is, the concentration of calcium carbonate in the source liquid solution is relatively high. The source liquid solution also preferably contains trace amounts of elements including, but are not limited to, Calcium, Titanium, Vanadium, Chromium, Manganese, Iron, Cobalt, Nickel, Copper, Zinc, Molybdenum, Silver, Cadmium, Gold, Platinum, and the like. If the source liquid is deficient in any desired mineral or elemental constituent, minerals and elemental constituents may be added to the source liquid prior to treatment in the low zeta potential crystal generator.

The currently preferred device for generating low zeta potential crystals is the "Turbu-Flow™" system, which is described above. Other devices for changing the zeta potential of crystals are known in the art or may be developed and used in methods and systems of the present invention.

Figure 5:
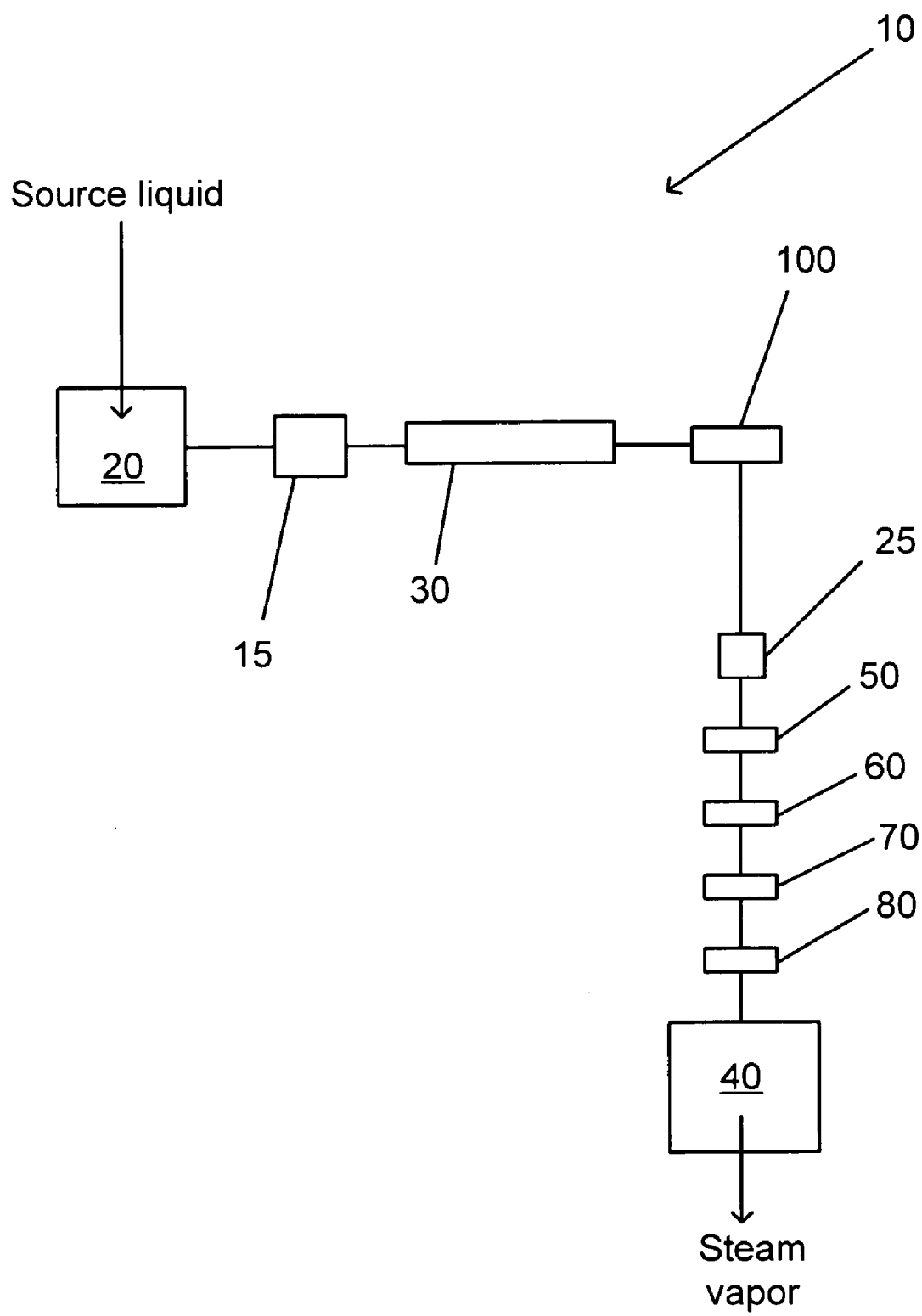

FIG. 5 shows an embodiment of a steam vapor generation system 10 for use in connection with disinfection and sterilization, comprising an optional source liquid pre-treatment system 15, a first low zeta potential crystal generator 30, an optional high zeta potential crystal generator 100, an optional pre-filtration system 50, an optional at least one filtration device 60, an optional second low zeta potential crystal generator 80, and a steam vapor generator 40. Pre-treatment system 15, low zeta potential crystal generator 30, high zeta potential crystal generator 100, pre-filtration system 50, filtration device 60, second low zeta potential crystal generator 80, and steam vapor generator 40 are in liquid communication with one another and are connected by way of a conduit system. The conduit system may include, for example, pipes, hoses, tubes, channels, and the like. The treated liquid may be stored or distributed via a steam vapor applicator for use in connection with disinfection and sterilization.

Any chelating agent, biocidal agent, fungicidal agent, surfactant, inorganic coagulant, polymeric coagulant, hydrophilic colloid known in the art may be added to or incorporated with the source liquid prior to treatment by the inventive system, the treated liquid, or the generated steam vapor.

Various types of steam vapor generator 40 may be used and are well known in the art for steam vapor generation. Pump 25 may be provided in line between low zeta potential crystal generator 30 and steam vapor generator 40 to provide a continuous or intermittent flow of liquid from the source, through low zeta potential crystal generator 30 and then to the steam vapor generator 40. Pump 25 may alternatively be provided downstream from the steam vapor generator 40 and between a steam generator outlet and steam vapor applicator.

Various control systems may be implemented for providing source liquid, monitoring and controlling the treatment process, and generating and applying steam vapor. Suitable control systems are well known in the art. Various types of steam vapor applicators may also be used with the methods and systems of the present invention to facilitate application of steam vapor to various types of surfaces, objects, and the like. Steam vapor applicators including hoses, pipes, ejectors, nozzles, valves, regulators, nylon brushes, stainless steel brushes, bristle brushes, soft clothes brushes, wall applicators, scrubbers, hydro brooms, foam pads, steam mops, steam pads, and the like may be used with the methods and systems of the present invention. In other embodiments, a plurality of steam applicators may be used with the methods and systems of the present invention.

Steam vapor generation system 10 uses source liquid solution having a concentration of calcium carbonate and/or other minerals sufficient to provide a source for generation of low zeta potential crystals. The source liquid solution, such as water, is supplied from any suitable source and may be stored in a reservoir 20, or may be supplied continuously or intermittently from any source. The composition of source liquid may be tested and, if necessary, additional minerals and other constituents may be added to provide a sufficient source for generation of low zeta potential crystals. The source liquid may also be treated, prior or subsequent to holding in reservoir 20, in pre-treatment system 15 to substantially remove unwanted contaminants that may interfere with the treatment process, such as debris, oil-containing constituents, and the like.

Source liquid may be added continuously or intermittently to liquid reservoir 20, and the liquid may be released using a passive system, or actively pumped, towards low zeta potential crystal generator 30. As described above, various systems are available for enhancing the zeta potential crystal concentration of liquids and any such systems may be used as low zeta potential crystal generator 30. Treated liquid is conveyed from low zeta potential crystal generator 30 to a steam generator 40, where the treated liquid is heated to form steam vapor, which is released intermittently or continuously for application to disinfect surfaces and/or objects. The low zeta potential crystals generated by low zeta potential crystal generator 30 do not settle readily and generally stay in suspension for a long period, even without agitation of the solution. Therefore, these low zeta potential crystals may be transported through the steam droplets generated via the steam generator 40 during the steam vapor production.

Treated liquid, after passage through low zeta potential crystal generator 30, contains a high concentration of low zeta potential crystals. In one embodiment, the zeta potential of mineral crystals in liquid following treatment in the low zeta potential crystal generator 30 is between 0 mV and −10 mV. In another embodiment, the zeta potential of mineral crystals in liquid following treatment in the low zeta potential crystal generator 30 is between −4 mV and −10 mV. In yet another embodiment, the zeta potential of mineral crystals in liquid following treatment in the low zeta potential crystal generator 30 is between −5 mV and −9 mV. The "plus" or "minus" signs of zeta potential measurements represent the positive or negative traveling direction of the mineral crystals, respectively, and do not relate to the actual value of the zeta potential. In other words, the value of zeta potential is irrespective of its "sign".

In another embodiment, the treated source liquid is optionally passed through at least one filtration device 60. In a preferred embodiment, filtration device 60 reduces or substantially eliminates bacteria, viruses, cysts, and the like. Any filtration devices known in the art may be used. Filtration device 60 may include, but is not limited to any of the following devices: particle filters, charcoal filters, reverse osmosis filters, active carbon filters, ceramic carbon filters, distiller filters, ionized filters, ion exchange filters, ultraviolet filters, back flush filters, magnetic filters, energetic filters, vortex filters, chemical oxidation filters, chemical addictive filters, Pi water filters, resin filters, membrane disc filters, microfiltration membrane filters, cellulose nitrate membrane filters, screen filters, sieve filters, or microporous filters, and combinations thereof. The treated and filtered liquid may be stored or distributed via a steam applicator for use in connection with disinfection and sterilization.

As shown in FIG. 5, before reaching steam generator 40, the treated liquid may optionally be passed through a high zeta potential crystal generator 100. High zeta potential crystal generators are known in the art and generally useful for prevention or reduction of scaling. In addition, high zeta potential crystal generator 100 keeps low zeta potential crystals generated by low zeta potential crystal generator 30 suspended in the treated liquid and will not reduce the zeta potential of the generated low zeta potential crystals. One known high zeta potential crystal generator 100 is the Zeta Rod® system. The Zeta Rod® system increases zeta potential of crystals by electronically dispersing bacteria and mineral colloids in liquid systems, eliminating the threat of bio-fouling and scale and significantly reducing use of chemical additives. Colloids in liquid systems become components of the capacitor and receive a strong boost to their natural surface charge, altering double-layer conditions that govern particle interactions. Mineral scale formation is prevented as the Zeta Rod® system stabilizes the dispersion of colloidal materials and suspended solids, preventing nucleation and attachment of scale to wetted surfaces. Bacteria remain dispersed in the bulk fluid rather than attaching to surfaces, and cannot absorb nutrition or replicate to form slime and create foul odors. Existing biofilm hydrates excessively, loses bonding strength and disperses. Also, biological fouling, biocorrosion, and scale formation are arrested by the Zeta Rod® system.

Another known high zeta potential crystal generator 100 is the Sterling Water Anti-Scale Appliance manufactured by Sterling Water Systems, LLC, a subsidiary of Porta Via Water Company. As water passes through the Sterling Water Anti-Scale Appliance, an electrical current is discharged into the water, which decreases the water's surface tension and inhibits the formation of scale and hard water spots from appearing. The inhibition of scale formation is due to the increase of zeta potential of the mineral crystals in the treated water, which keeps mineral particles from coming in contact with one another.

As shown in FIG. 5, after passage through low zeta potential crystal generator 30 and the optional high zeta potential crystal generator 100, and before reaching the optional at least one filtration device 60, the treated liquid may optionally be passed through pre-filtration system 50, wherein minerals, such as iron, sulphur, manganese, and the like are substantially removed from the treated source liquid. Pre-filtration system 50 can be, for example, a stainless steel mesh filter. The treated and pre-filtered source liquid, is next passed through the optional at least one filtration device 60, wherein bacteria, viruses, cysts, and the like are substantially removed from the treated liquid.

The treated liquid, containing a high concentration of low zeta potential crystals, may be distributed to and stored in a storage container 70, such as a reservoir. In this embodiment, before distribution of the stored treated liquid, the stored liquid may be passed through a second low zeta potential crystal generator 80, for generation of additional low zeta potential crystals in the treated source liquid. The twice treated liquid may then be distributed to steam generator 40 to produce steam vapor containing an enhanced concentration of low zeta potential crystals.

It has also been observed that liquid treated by the system 10 inhibits and reverses the growth of biofilm. It is thought that the change in crystal structure and concentration in the treated steam vapor leaves no place to the microorganisms to attach. Also, the change in zeta potential modifies the interaction between particles and cell membrane because the nano size low zeta potential crystals could cross the cell membrane of the microorganisms and destroy the cell.

Applications of the Inventive System

Systems of the present invention equipped with a low zeta potential crystal generator 30, such as the Turbu-Flow™ system and a steam vapor generator 40, and may be used for disinfection and sterilization of objects, hard and soft surfaces, devices, and environments, including, but not limited to, autoclaves, autos and boats, bathrooms (toilets, tiles, cervices, showers, bathtubs, sinks, sink counters, shower doors, glass surfaces, mirrors), floors (rugs, stairs, edges, linoleum surfaces, hardwood floors, tiled floors), carpets, glass, mini-blinds, window tracks, walls, kitchens (ovens and oven racks, microwave ovens, ice makers, appliances such as refrigerators, can openers, toasters, and grills), outdoors (mats, awnings, bricks, sidings), enclosed spaces (autoclaves, sterilizer), sport equipments, upholstery, furniture, bedding, mattresses, toys, personal belongings, and the like, in residential, commercial, industrial, recreational, hospitals, and medical and dental facilities.

EXAMPLE 1

Chemical Analysis of Untreated and "Turbu-Flow™" Treated Water

A chemical analysis comparing the wet chemistry and elemental metal composition of untreated, "raw" water and water treated in a low zeta potential generator, such as the Turbu-Flow™ system is shown below in Table 1. The instrument detection limits are also provided. According to the results shown in Table 1, very little change can be detected in treated water, except that an increase in turbidity (a measure of the cloudiness of water caused by suspended particles) is observed.

TABLE 1

| | | Instrument Detection Limit | Untreated Water | Treated Water |
|---|---|---|---|---|
| Wet Chem. | Conductivity (us/cm) | 3 | 720 | 720 |
| | pH (pH units) | 0.1 | 7.8 | 7.7 |
| | Turbidity (NTU) | 0.10 | 0.30 | 0.50 |
| Metals | Aluminum (mg/L) | 0.01 | 0.02 | 0.02 |
| | Barium (mg/L) | 0.01 | 0.08 | 0.08 |
| | Beryllium (mg/L) | 0.001 | <0.001 | <0.001 |
| | Boron (mg/L) | 0.05 | <0.05 | <0.05 |
| | Cadmium (mg/L) | 0.0001 | <0.0001 | <0.0001 |
| | Calcium (mg/L) | 0.5 | 84 | 85 |
| | Chromium (mg/L) | 0.001 | 0.001 | 0.001 |
| | Cobalt (mg/L) | 0.0008 | <0.0008 | <0.0008 |
| | Copper (mg/L) | 0.001 | 0.059 | 0.052 |
| | Iron (mg/L) | 0.05 | 0.11 | 0.11 |
| | Lead (mg/L) | 0.001 | <0.001 | <0.001 |
| | Magnesium (mg/L) | 0.5 | 20 | 20 |
| | Manganese (mg/L) | 0.001 | 0.004 | 0.004 |
| | Molybdenum (mg/L) | 0.001 | <0.001 | <0.001 |
| | Nickel (mg/L) | 0.002 | <0.002 | <0.002 |
| | Potassium (mg/L) | 0.5 | 1.9 | 1.9 |
| | Silver (mg/L) | 0.0001 | <0.0001 | <0.0001 |
| | Sodium (mg/L) | 0.5 | 19 | 20 |
| | Strontium (mg/L) | 0.001 | 0.24 | 0.24 |
| | Thallium (mg/L) | 0.0003 | <0.0003 | <0.0003 |
| | Uranium (mg/L) | 0.005 | <0.005 | <0.005 |
| | Vanadium (mg/L) | 0.001 | 0.003 | 0.003 |
| | Zinc (mg/L) | 0.003 | 0.004 | 0.004 |
| | Zirconium (mg/L) | 0.001 | <0.001 | <0.001 |

EXAMPLE 2

Testing Antimicrobial Action of Treated Steam Vapor on Hard Surfaces

The following table illustrates the results of surface treatment using an embodiment the inventive steam vapor system 10 ("MondoVap 2400 steam vapor system") equipped with a low zeta potential crystal generator, such as the Turbu-Flow™ system. The population of microorganisms present on the surface is eliminated by a log factor of 6-7 after relatively short duration exposure to the steam vapor. The exposure time to steam vapor are as follows: application 1=7 seconds; application 2=10 seconds; application 3=30 seconds.

This experiment describes the procedures for determining the effectiveness of the MondoVap 2400 steam vapor system equipped with a low zeta potential crystal generator tested against representative challenge microorganisms. The steam vapor system was tested against designated microorganisms that were dried onto a representative porous coupon surface. Each combination was tested in duplicate with positive controls against the organisms listed below.

Test Microorganism Preparation:

Microorganisms were inoculated into the appropriate media and grown according to the following table:

TABLE 2

| ORGANISM | MEDIA | TEMPERATURE | TIME |
|---|---|---|---|
| *Staphylococcus aureus* ATCC #6538 | SCDB | 30-35° C. | 24-48 Hours |
| *Staphylococcus epidermidis* ATCC #12228 | SCDB | 30-35° C. | 24-48 Hours |
| *Pseudomonas aeruginosa* ATCC #15442 | SCDB | 30-35° C. | 24-48 Hours |

TABLE 2-continued

| ORGANISM | MEDIA | TEMPERATURE | TIME |
|---|---|---|---|
| *Escherichia coli* ATCC #8739 | SCDB | 30-35° C. | 24-48 Hours |
| *Enterococcus faecium* ATCC #19434 | SCDB | 30-35° C. | 24-48 Hours |
| *Listeria monocytogenes* ATCC #19111 | SCDB | 30-35° C. | 24-48 Hours |
| *Salmonella choleraesuis* ATCC #10708 | SCDB | 30-35° C. | 24-48 Hours |

The *P. aeruginosa* test culture was decanted aseptically leaving the pellicle behind.

*C. albicans* ATCC #10231 was transferred to plates of Sabouraud dextrose agar (SDEX) and incubated at 20-25° C. for 3-4 days. The culture was harvested with Physiological Saline Solution 0.9% (PHSS).

*A. niger* ATCC #16404 was inoculated onto Sabouraud dextrose agar (SDEX) and incubated at 20-25° C. for 6-10 Days. *A. niger* was harvested by removing the mycelial mats from the surface using a sterile spatula. The mycelia were placed into a sterile funnel containing moist cotton and rinsed with SALT, a solution of 0.9% saline with 0.05% Tween.

*T. mentagrophytes* ATCC #9533 was inoculated onto plates of glucose agar (FUAGA) and incubated at 25-30° C. for 6-10 days. The mycelial mats were removed from the agar surface using a sterile spatula. The mycelia were transferred to a sterile tissue grinder and macerated using PHSS. The suspension was filtered through a sterile funnel containing moist cotton and standardized with PHSS.

Test Product Preparation:

A MondoVap 2400 steam vapor system was modified by installing a low zeta potential crystal generator such as the Turbu-Flow™ system in the liquid conduit between the water reservoir and the steam vapor generator.

Coupon Preparation:

Clay tile coupons were sterilized in an autoclave at 121+° C. for a minimum of 20 minutes. Coupons were prepared in duplicate for each organism/product application. Additional coupons were prepared to represent positive and negative coupons.

Test Procedure:

The prepared cultures of each test microorganism were thoroughly shaken. Coupons were inoculated with 0.01-0.03 mL of prepared culture. The culture was immediately spread uniformly over an approximate "×1" area. Two positive control coupons were inoculated for each microorganism and surface type. The negative control coupons were left uninoculated. The coupons were dried for 30-40 minutes at 37+/−2° C. Positive control coupons were immediately transferred to 100 mL of Letheen broth (LETH) after the drying time. Three applications were performed as follows:

Application One: A nozzle brush with a towel placed over the brush was applied to the coupon. The brush was placed on coupons with a back and forth motion while steam from the modified MondoVap 2400 steam vapor system was activated. The exposure time for application one was 7 seconds.

Application Two: The Tri-brush with a towel placed over the brush was applied to the coupon. The brush was placed on coupons with a back and forth motion while steam from the modified MondoVap 2400 steam vapor system was activated. The exposure time for the application was 10 seconds.

Application Three: The Tri-brush with a towel placed over the brush was applied to the coupon. The brush was placed on coupons with a back and forth motion while steam from the modified MondoVap 2400 steam vapor system was activated. The exposure time for the application was 30 seconds.

After the exposure time, the coupons were placed into 100 mL of LETH. The bottles were shaken manually for 1 minute or 100 times through a 12 inch path to extract surviving organism. The positive controls were extracted in the same manner. After the first extraction of the positive controls, the coupons were transferred to new bottles containing 100 mL of LETH and a second extraction was performed. This was repeated a third time. Appropriate dilutions of the positive controls were made in LETH to achieve plates within a countable range. The extract was serially diluted in LETH blanks. Plate counts were performed in triplicate by plating 0.5 mL onto appropriate agar. The remaining extraction fluid was filtered through a sterile 0.45 pm filter membrane to determine total kill. The filter was plated onto the appropriate agar. Soybean casein digest agar (SCDA) for bacteria samples, Sabouraud Dextrose Agar (SDEX) for yeast and mold, and 1% Glucose Agar (FUAGA) was used for fungus. Bacterial samples were incubated at 30-35° C. for 48-72 hours. Mold test samples were incubated at 20-25° C. for 3-7 days. Yeast test samples were incubated at 20-25° C. for 3-5 days. Fungi samples were incubated at 25-30° C. for 4-10 days. The test procedures were repeated for all possible organism and cleaning application combinations.

Calculations:

For the positive controls, the percent efficiency is obtained by dividing the number of microorganisms recovered in the first extraction by the total number of microorganisms recovered from the coupon over all three extractions. The positive control titer is corrected for the percent efficiency by dividing the number recovered in the first extraction by the percent efficiency.

Log reductions were calculated using the following formula:

$$\text{log reduction} = \log U - \log C$$

Where U=Average corrected positive control titer

Where C=Average corrected recovered counts

Percent reductions were calculated using the following formula:

$$\% \text{ reduction} = 1 - \frac{1}{10^{(\log \text{ reduction})}} \times 100\%$$

Acceptance Criteria:

In order to be considered passing for each surface, the application(s) must demonstrate a 3 log reduction against vegetative organisms and at least a 2 log reduction against spore forming organisms.

Results:

The counts of various recovered microorganisms, including bacteria and spores, percent reductions and log, reductions for the test materials are shown in Table 3 below. The data in Table 3 demonstrates effective kill for the microorganism types and applications in 7 seconds with some microorganisms demonstrating even greater kill at 10 and 30 seconds.

*S. aureus* is a spherical bacterium (coccus) which on microscopic examination appears in pairs, short chains, or bunched, grape-like clusters. These microorganisms are Gram-positive. Some strains are capable of producing a highly heatstable protein toxin that causes illness in humans. *S. epidermidis*, appears as white colonies on sheep blood agar plates. Both *S. aureus* and *S. epidermidis* are normal inhabitants of the skin. *P. aeruginosa* is a versatile Gram-negative bacterium that grows in soil, marshes, and coastal marine habitats, as well as on plant and animal tissues. *S. choleraesuis* is a host adapted, facultative intracellular pathogen that causes swine paratyphoid. *E. coli* is a bacterial species which inhabits the intestinal tract of man and other warm-blooded animals. *L. monocytogenes* is a gram-positive, motile, rod-shaped bacterium that is found principally in contaminated food products. *E. Faecium* is gram-positive, spherical bacteria that colonize in groups or chains. They are naturally found as part of the digestive tract flora in many organisms, including humans. An *E. Faecium* infection can cause complicated abdominal infections, skin and skin structure infections, urinary tract infections and infections of the blood stream. *C. albicans* is the most frequently isolated fungal pathogen of humans, affecting immuo-compromised patients ranging from premature infants to AIDS sufferers. Spores of the above mentioned bacteria can be formed in response to adverse changes in the environment.

The results in Table 3 show that surfaces treated by steam vapor produced by the modified Mondo Vap 2400 steam vapor system installed with a Turbu-Flow™ low zeta potential crystal generator system and demonstrate dramatic reduction and substantial elimination of various bacteria and spores on surfaces. These organisms are not readily eliminated from these types of surfaces by thermal steam alone.

TABLE 3

| Organism | Application | Percent reduction | $Log_{10}$ reduction |
|---|---|---|---|
| S. aureus | 1 | 99.89 | 2.95 |
|  | 2 | 99.999996 | 7.40 |
|  | 3 | 99.999996 | 7.40 |
| S. epidermidis | 1 | 99.999991 | 7.04 |
|  | 2 | 99.999991 | 7.04 |
|  | 3 | 99.999991 | 7.04 |
| P. aeruginosa | 1 | 99.999994 | 7.26 |
|  | 2 | 99.999994 | 7.26 |
|  | 3 | 99.999994 | 7.26 |
| S. choleraesuis | 1 | 99.999993 | 7.15 |
|  | 2 | 99.999993 | 7.15 |
|  | 3 | 99.999993 | 7.15 |
| E. coli | 1 | 99.999994 | 7.26 |
|  | 2 | 99.999931 | 6.16 |
|  | 3 | 99.999994 | 7.26 |
| L. monocytogenes | 1 | 99.99966 | 5.47 |
|  | 2 | 99.999978 | 6.66 |
|  | 3 | 99.999924 | 6.12 |
| E. Faecium | 1 | 99.999995 | 7.32 |
|  | 2 | 99.999995 | 7.32 |
|  | 3 | 99.999995 | 7.32 |
| C. albicans | 1 | 99.999993 | 7.15 |
|  | 2 | 99.999993 | 7.15 |
|  | 3 | 99.999997 | 7.46 |

EXAMPLE 3

Kill Time Study

The following table illustrates the kinetics of the destruction of microorganisms using steam vapor application according to the present invention. This example shows that regular tap water treated by the Turbu-Flow system results in an equivalent level of decontamination as sterile, deionized water.

Inoculum Preparation:

Cultures of *S. aureus* ATCC #6538 and *L. monocytogenes* ATCC #19111 were transferred from stock cultures to individual tubes of Soybean casein digest broth (SCDB) media. Cultures were incubated at 30-35° C. for 24-48 hours.

*A. niger* ATCC #16404 was inoculated onto Sabouraud dextrose agar (SDEX) and incubated at 20-25° C. for 6-10 days. *A. niger* was harvested by removing the mycelial mats from the surface using a sterile spatula. The mycelia were placed into a sterile funnel containing moist cotton and rinsed with SALT, a solution of 0.9% saline with 0.05% Tween. Organism concentration was adjusted in Physiological Saline Solution (PHSS) to produce a challenge level of approximately $10^{6-7}$ CFU/mL using visual turbidity.

*A. niger* is a fungus commonly found on textiles, in soils, grains, fruits, and vegetables and is a common cause for skin, pulmonary, and ear infections. *S. aureus* is a spherical bacterium and a common inhabitant of human skin. *L. monocytogenes* is a gram-positive, motile, rod-shaped bacterium that is found principally in contaminated food products.

Sample Preparation:

Samples were tested as received without any additional dilution or manipulation.

Test Procedure:

Tubes containing 9 mL of each test sample were brought to 50+/−2° C. in a waterbath. One mL of the prepared test microorganism suspension was added to each tube containing the test sample to yield a minimum of $1\times10^5$ CFU/mL challenge microorganism. The samples were mixed by swirling. The tubes were placed back into the waterbath. At 50° C., 60° C., 70° C., 80° C., and 90° C. (all temperatures within +2° C.) exposure temperatures 1.0 mL aliquots of sample solution-cell suspension were removed and added to 9 mL of Letheen broth (LETH). The tubes were mixed thoroughly. Ten-fold serial dilutions were made in blanks containing 9 mL of LETH through the appropriate dilution. Triplicate aliquots were plated from selected dilutions onto Soybean casein digest agar (SCDA) for *S. aureus* and *L. monocytogenes* samples and SDEX for *A. niger* samples. Bacterial plates were incubated at 30-35° C. for 48-72 hours and mold plates were incubated at 20-25° C. for 3-7 days.

Positive Control:

Tubes were prepared containing 9 mL of sterile deionized water at 200 ppm hard water for each organism type. The tubes were equilibrated to 50±2° C. At T=0, 1 mL of test organism was added to the tube. Aliquots of the control were removed at the same temperature and relative time points as the test sample. Ten-fold serial dilutions were prepared in dilution blanks containing 9 mL of LETH. Triplicate aliquots were plated from selected dilutions onto Soybean casein digest agar (SCDA) for *S. aureus* and *L. monocytogenes* samples and SDEX for *A. niger* samples. Bacterial plates were incubated at 30-35° C. for 48-72 hours and mold plates were incubated at 20-25° C. for 3-7 days.

Acceptance Criteria:

Positive controls must demonstrate a titer of ≧10.5 CFU/mL. Negative controls must not show any growth of the test organism.

Results:

The percent reduction and log reduction results in Table 4 show that tap water treated in the Turbu-Flow™ system to produce water having a high concentration of low zeta potential crystals has at least the equivalent ability to reduce growth of various fungi, bacteria and spores as deionized water.

Negative controls did not show growth of the test microorganisms. The data as shown in Table 4 also demonstrates that tap water treated by the Turbu-Flow system has superior ability to reduce growth of microorganisms than that of deionized water at lower temperature (50° C.).

TABLE 4

| Organism | Temperature | Percent reduction | $Log_{10}$ reduction |
|---|---|---|---|
| A. niger | 50° C. | 47 | 0.28 |
| Treated water | 60° C. | 81 | 0.72 |
| | 70° C. | 99.9989 | 4.97 |
| | 80° C. | 99.9989 | 4.97 |
| | 90° C. | 99.9989 | 4.97 |
| A. niger | 50° C. | 0 | 0 |
| Deionised water | 60° C. | 84 | 0.8 |
| (Control) | 70° C. | 99.9989 | 4.57 |
| | 80° C. | 99.9989 | 4.97 |
| | 90° C. | 99.9989 | 4.97 |
| S. aureus | 50° C. | 20 | 0.1 |
| Treated water | 60° C. | 56 | 0.36 |
| | 70° C. | 99.9956 | 4.36 |
| | 80° C. | 99.99959 | 5.39 |
| | 90° C. | 99.99959 | 5.39 |
| S. aureus | 50° C. | 0 | 0 |
| Deionised water | 60° C. | 99.959 | 3.39 |
| (Control) | 70° C. | 99.99959 | 5.39 |
| | 80° C. | 99.99904 | 5.02 |
| | 90° C. | 99.99959 | 5.39 |
| L. monocytogenes | 50° C. | −310 | −0.61 |
| Treated water | 60° C. | 37 | 0.20 |
| | 70° C. | 99.989 | 3.97 |
| | 80° C. | 99.989 | 3.97 |
| | 90° C. | 99.989 | 3.97 |
| L. monocytogenes | 50° C. | 0 | 0 |
| Deionised water | 60° C. | 98.9 | 1.97 |
| (Control) | 70° C. | 99.989 | 3.97 |
| | 80° C. | 99.989 | 3.97 |
| | 90° C. | 99.989 | 3.97 |

EXAMPLE 4

Water Surface Tension Analysis

Samples of untreated water and water treated by passage through a low zeta potential crystal generator were generated and analyzed for surface tension at room temperature and at 80° C. The results of the analysis are summarized in Table 5.

TABLE 5

| | Untreated Water | | Turbu-Flow Treated Water | |
|---|---|---|---|---|
| Date | Room Temp | 80° C. | Room Temp | 80° C. |
| May 5, 2004 | 79.0 dynes/cm | na | 69.5 dynes/cm | na |
| May 25, 2004 | 79.1 dynes/cm | 69.2 dynes/cm | 77.4 dynes/cm | 67.5 dynes/cm |

Table 5 shows a dramatic decrease in water surface tension after a single pass through the Turbu-Flow system. The sample was analyzed approximately one week later. Based on a one-week-old sample, the surface tension dropped from 79.0 dynes/cm in the untreated water to 69.3 dynes/cm in the water treated by the Turbu-Flow system.

To further delineate the impact of time and temperature on the surface tension, the analysis was repeated almost three weeks later. At this time, the treated water sample exhibited only a slight decrease in surface tension over the untreated water at both room temperature and at 80° C. This analysis demonstrates that water treated by the Turbu-Flow system will revert back to its original surface tension over time. The most significant findings of this experiment is that for a period of more than a week after the water sample is passed through the Turbu-Flow system, it exhibited a surface tension that is similar in magnitude to water that has been heated to 80° C.

Thus, the water treated by the Turbu-Flow system has the ability to cause microorganisms to be less heat-tolerant due to the lower surface tension of the treated water.

EXAMPLE 5

Comparison of Water Characteristics over Time

On Jul. 19, 2004, a sample of tap water treated by the Turbu-Flow system from Jun. 29, 2004 was submitted for analysis along with a tap water sample treated by passage through a Turbo-Flow system on Jul. 19, 2004. The results of these analyses are summarized in Table 6 below.

TABLE 6

| | Treated - June 29 | Initial Tap Water July 19$^{th}$ | Treated - July 19$^{th}$ |
|---|---|---|---|
| pH (pH units) | 6.63 | 7.89 | 7.16 |
| Turbidity (NTU) | 0.91 | 0.17 | 0.45 |
| Colour - Apparent (TCU) | <1 | 1 | 5 |

The results in Table 6 demonstrate that water treated by the Turbu-Flow system collected on Jun. 29, 2004 had a significantly depressed pH compared to the untreated and treated samples of Jul. 19, 2004. Also, the turbidity and the color of the three week old treated water sample are higher than that of the untreated water. The increase in turbidity and color of a three week old water sample that was treated by the Turbu-Flow system had not been previously observed.

EXAMPLE 6

Continuous Spray Test with Untreated and Treated Water

A continuous spray test with treated and untreated water was performed in April 2005. A shower curtain was hung in a 4 foot diameter cooling tower barrel. On one side of the curtain, Turbu-Flow™ treated city water was continuously distributed via 6 spray nozzles, and on the other side of the curtain, untreated city water was continuously distributed via 6 spray nozzles. Swabs were taken weekly to count microorganism levels. At the end period, the samples from the treated side did not have enough microorganisms to measure. The untreated side was saturated with microorganisms. This test showed that city water treated by the Turbu-Flow™ system cannot grow microorganisms, while untreated water will encourage the growth of microorganisms.

EXAMPLE 7

Mold Carpet Study

A study was conducted to evaluate the growth of fungi and its removal in wetted carpet over time using methods and systems of the present invention. Sixty samples of carpet were imbedded with heat-treated house dust, followed by imbedding, wearing with a hexapod, wetting and inoculation with a liquid suspension of *Cladosporium sphaerospermum* prior to placement over a water-saturated foam pad and incubated for 24 hours, 7 days, and 30 days. Cleaning was performed using three methods; high-flow and hot water extraction, hot water and detergent, and application of steam vapor produced by methods and systems of the present invention. Fungal loading increased from approximately 1,300 colony forming units (CFU) per square feet in 24 hours to a maximum of approximately 9,200 colony forming units per square feet after seven days with a slight decline in growth after 30 days incubation. Significant differences were found among all three methods for removal of fungi over time (p<0.05). Application of steam vapor produced by methods and systems of the present invention was significantly better than the other two methods (p<0.001) with 99% efficiency in removal of *Cladosporium sphaerospermum* from wetted carpet after 24 hours and 30 days incubation time, with 92% efficiency after 7 days. The other two methods had declining efficiencies of fungal removal over time, from a maximum of 82% and 81% at 24 hours down to 60% and 43% at 30 days for hot water and detergent and high-flow and hot water methods, respectively. The net effect of the mold management study demonstrates that while application of steam vapor produced by methods and systems of the present invention has a nearly constant fungal removal rate, the hot water and detergency and high-flow and hot water methods declined in efficiency with increasing fungal growth.

EXAMPLE 8

Virucidal Effectiveness Test—Feline Calicivirus (Surrogate for Norwal and Norwalk-lke Viruses) on Unglazed, Clay Tiles Using the Dry Steam Vapor System 2400 Series in accordance with systems and methods of the present invention with a low zeta potential crystal generator between liquid source and the steam vapor system's nozzle brush and towel placed over the brush head, steam vapor was applied to the carrier (unglazed clay tiles) containing feline calicivirus (Host: Crandell feline kidney (CrFK) cells, American BioResearch Laboratories), using back and forth motion for 7 and 10 seconds. Duplicate carriers were treated individually at each time point.

Results:

Results are presented in Tables 7-10 below. A titration was performed to determine the titer of the viral stock. The cell culture infective dose 50% per mL (CCID50/mL) was determined from the virus stock, test, and tile recovery data using the method of Reed and Muench, 1938. The cell viability control demonstrated CrFK cell viability and media sterility. Virus was not recovered in the cell viability control. Neither the steam-treated tile nor tile alone was cytotoxic to the assay system. The lower limit of viral detection for this test system is at 101.50 infectious units per mL.

TABLE 7

Test Results

| | Virus Tile Recovery | Contact Time | | | |
|---|---|---|---|---|---|
| | | 7 Sec. | | 10 Secs. | |
| Dilutions($\log_{10}$) | Control | Tile 1 | Tile 2 | Tile 1 | Tile 2 |
| $10^{-2}$ | ++++ | 0000 | 0000 | 0000 | 0000 |
| $10^{-3}$ | ++++ | 0000 | 0000 | 0000 | 0000 |
| $10^{-4}$ | ++++ | 0000 | 0000 | 0000 | 0000 |
| $10^{-5}$ | 0+0+ | 0000 | 0000 | 0000 | 0000 |
| $10^{-6}$ | 0++0 | 0000 | 0000 | 0000 | 0000 |

TABLE 7-continued

Test Results

| | Virus Tile Recovery | Contact Time | | | |
|---|---|---|---|---|---|
| | | 7 Sec. | | 10 Secs. | |
| Dilutions($\log_{10}$) | Control | Tile 1 | Tile 2 | Tile 1 | Tile 2 |
| $10^{-7}$ | 0000 | 0000 | 0000 | 0000 | 0000 |
| $CCID_{50}$/ml | $10^{5.50}$ | $\leq10^{1.50}$ | $\leq10^{1.50}$ | $\leq10^{1.50}$ | $\leq10^{1.50}$ |

Keys:
+ = Feline calicivirus infected cells were detected, cytopathic effects observed
0 = Feline calicivirus infected cells not detected, no cytopathic effects observed; no cytotoxicity observed.

TABLE 8

Log Reduction Summary

| Contact Time | Tile Replicate | $CCID_{50}$/ml | Log 10 Reduction from Virus tile recovery control |
|---|---|---|---|
| 7 Secs. | Tile 1 | $\leq10^{1.50}$ | $\geq4.00$ |
| 7 Secs. | Tile 2 | $\leq10^{1.50}$ | $\geq4.00$ |
| 10 Secs. | Tile 1 | $\leq10^{1.50}$ | $\geq4.00$ |
| 10 Secs. | Tile 2 | $\leq10^{1.50}$ | $\geq4.00$ |

TABLE 9

Neutralizer Effectiveness and Cytotoxicity Related Controls

Dry Steam Vapor System, 2400 Series

| Dilution | Neutralizer Effectiveness | Cytotoxicity Control | Cytotoxicity-related Viral Interference Control |
|---|---|---|---|
| $10^{-2}$ | ++++ | 0000 | ++++ |
| $10^{-3}$ | ++++ | 0000 | ++++ |
| $10^{-4}$ | ++++ | 0000 | ++++ |

Keys:
+ = Feline calicivirus infected cells were detected, cytopathic effects observed
0 = Feline calicivirus infected cells not detected, no cytopathic effects observed; no cytotoxicity observed.

TABLE 10

Control Results

| Dilution | Tile Carrier Cytotoxicity Control |
|---|---|
| $10^{-1}$ | 0000 |
| $10^{-2}$ | 0000 |
| $10^{-3}$ | 0000 |
| $CCID_{50}$/ml | $\leq10^{1.50}$ |
| Dilution | Cell Viability/Media Control |
| $10^{0}$ | 0000 |

Keys:
+ = Feline calicivirus infected cells were detected, cytopathic effects observed
0 = Feline calicivirus infected cells not detected, no cytopathic effects observed; no cytotoxicity observed.
C = Cytotoxicity Observed

CONCLUSIONS

When tested as described, Dry Steam Vapor System 2400 Series passed the Virucidal Effectiveness Test when Feline calicivirus surrogate for Norwalk Virus, containing at least a 5% organic load, was exposed to the test agent for 7 seconds or for 10 seconds. These conclusions are based on observed data.

While certain embodiments of the present invention have been described, it will be understood that various changes could be made in the above constructions without departing from the scope of the invention. It is intended that all matter contained in the above description or shown in the accompanying drawings shall be interpreted as illustrative and not in a limiting sense.

I claim:

1. A method for disinfecting and sterilizing a surface, an object, or an environment by reducing or substantially eliminating microorganisms, comprising:
    passing source liquid through a low zeta potential crystal generator and thereby producing treated liquid having an enhanced concentration of low zeta potential crystals;
    passing the treated liquid through a high zeta potential crystal generator and thereby producing treated liquid having an enhanced concentration of high zeta potential crystals;
    passing the treated liquid though a steam vapor generator to generate steam vapor from the treated liquid; and
    applying or distributing the steam vapor containing an enhanced concentration of low zeta potential crystals and an enhanced concentration of high zeta potential crystals by way of a steam vapor applicator to the surface, the object, or the environment, thereby reducing or substantially eliminating microorganisms which are not readily destructible by thermal steam alone.

2. The method of claim 1, wherein the zeta potential of mineral crystals in the treated liquid after passage though the low zeta potential crystal generator is at least 25% less than the zeta potential of mineral particles in the source liquid.

3. The method of claim 1, wherein the zeta potential of mineral crystals in the treated liquid after passage through the low zeta potential crystal generator is at least 50% less than the zeta potential of mineral particles in the source liquid.

4. The method of claim 1, wherein the zeta potential of mineral crystals in the treated liquid after passage through the low zeta potential crystal generator is between about −5 mV and −9 mV.

5. The method of claim 1, further comprising passing the treated liquid through at least one filtration system to reduce the concentration of microorganisms in the treated liquid, thereby producing treated liquid having an enhanced concentration of low zeta potential crystals, an enhanced concentration of high zeta potential crystals, and reduced microbial populations.

6. The method of claim 5, further comprising passing the treated liquid through a pre-filtration system for substantially removing minerals from the treated liquid source prior to treatment in the at least one filtration device, wherein the minerals are selected from the group consisting of: iron, sulphur, manganese, and combinations thereof.

7. The method of claim 1, further comprising passing the source liquid through a pre-treatment system, wherein the pre-treatment system substantially removes contaminants from the source liquid prior to treatment in the low zeta potential crystal generator or receives additives to introduce to the source liquid prior to treatment in the low zeta potential crystal generator.

8. The method of claim 1, further comprising passing the treated liquid through a second low zeta potential crystal generator.

9. The method of claim 1, wherein the steam vapor applicator is selected from the group consisting of: hoses, pipes, ejectors, nozzles, valves, regulators, nylon brushes, stainless steel brushes, bristle brushes, soft clothes brushes, wall applicators, scrubbers, hydro brooms, foam pads, steam mops, steam pads, and combinations thereof.

10. A system for disinfecting or sterilizing a surface, an object, or an environment, comprising:
    a source liquid input;
    a low zeta potential crystal generator in liquid communication with the source liquid input for generating treated liquid having an enhanced concentration of low zeta potential crystals;
    a steam vapor generator in liquid communication with the low zeta potential crystal generator for generating steam vapor containing an enhanced concentration of low zeta potential crystals;
    a high zeta potential crystal generator in liquid communication with the low zeta potential crystal generator and the steam vapor generator; and
    a steam vapor applicator in communication with the steam vapor generator and adapted to facilitate application of steam vapor containing an enhanced concentration of low zeta potential crystals and an enhanced concentration of high zeta potential crystals to the surface, the object or the environment, thereby reducing or substantially eliminating microorganisms which are not readily destructible by thermal steam alone.

11. The system of claim 10, wherein the low zeta potential crystal generator is capable of reducing the zeta potential of mineral particles in source liquid by at least 25%.

12. The system of claim 10, wherein the low zeta potential crystal generator is capable of reducing the zeta potential of mineral particles in source liquid by at least 50%.

13. The system of claim 10, wherein the low zeta potential crystal generator is capable of producing treated water having a zeta potential of between about −5 mV and −9 mV for introduction to the steam vapor generator.

14. The system of claim 10, further comprising at least one filtration system in liquid communication with the low zeta potential crystal generator.

15. The system of claim 14, further comprising a pre-filtration system in liquid communication with the low zeta potential crystal generator and the at least one filtration system.

16. The system of claim 10, further comprising a pre-treatment system in liquid communication with the source liquid input.

17. The system of claim 10, further comprising a second low zeta potential crystal generator in liquid communication with the low zeta potential crystal generator.

18. The system of claim 10, wherein the steam vapor applicator is selected from the group consisting of: hoses, pipes, ejectors, nozzles, valves, regulators, nylon brushes, stainless steel brushes, bristle brushes, soft clothes brushes, wall applicators, scrubbers, hydro brooms, foam pads, steam mops, steam pads, and combinations thereof.

* * * * *